United States Patent
Nakamura

(10) Patent No.: US 12,374,443 B2
(45) Date of Patent: Jul. 29, 2025

(54) DOCUMENT CREATION SUPPORT APPARATUS, DOCUMENT CREATION SUPPORT METHOD, AND PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 381 days.

(21) Appl. No.: 17/752,876

(22) Filed: May 25, 2022

(65) Prior Publication Data

US 2022/0285011 A1    Sep. 8, 2022

Related U.S. Application Data

(63) Continuation of application No. PCT/JP2020/044239, filed on Nov. 27, 2020.

(30) Foreign Application Priority Data

Nov. 29, 2019 (JP) .................................. 2019-217420

(51) Int. Cl.
| | |
|---|---|
| G16H 30/40 | (2018.01) |
| G06F 40/169 | (2020.01) |
| G06F 40/56 | (2020.01) |
| G06T 7/00 | (2017.01) |
| G06V 10/764 | (2022.01) |

(52) U.S. Cl.
CPC ........... *G16H 30/40* (2018.01); *G06F 40/169* (2020.01); *G06F 40/56* (2020.01); *G06T 7/0012* (2013.01); *G06V 10/764* (2022.01)

(58) Field of Classification Search
CPC ....... G16H 30/40; G06F 40/169; G06F 40/56; G06T 7/0012; G06V 10/764
See application file for complete search history.

(56) References Cited

U.S. PATENT DOCUMENTS

| | | | |
|---|---|---|---|
| 5,807,256 A | | 9/1998 | Taguchi et al. |
| 9,582,482 B1 * | | 2/2017 | Sharifi ................ G06F 3/04845 |
| | (Continued) | | |

FOREIGN PATENT DOCUMENTS

| | | |
|---|---|---|
| JP | H0731591 | 2/1995 |
| JP | 2012053632 | 3/2012 |
| | (Continued) | |

OTHER PUBLICATIONS

"Office Action of Japan Counterpart Application", issued on Jun. 6, 2023, with English translation thereof, pp. 1-5.

(Continued)

*Primary Examiner* — Amandeep Saini
*Assistant Examiner* — Emma Rose Goebel
(74) *Attorney, Agent, or Firm* — JCIPRNET

(57) ABSTRACT

A document creation support apparatus comprises at least one processor. The processor is configured to generate a first text describing a property of a feature portion for each of a plurality of feature portions included in an image, classify the plurality of feature portions into at least one group, generate a second text integrating the first text generated for each of the feature portions belonging to the same group for each group, and generate a third text integrating the second text generated for each group.

13 Claims, 13 Drawing Sheets

(56) References Cited

U.S. PATENT DOCUMENTS

| | | | | |
|---|---|---|---|---|
| 2003/0159113 | A1* | 8/2003 | Bederson | G06F 40/20 |
| | | | | 715/252 |
| 2012/0166219 | A1* | 6/2012 | Mansour | G16H 10/60 |
| | | | | 705/3 |
| 2013/0290826 | A1 | 10/2013 | Niwa et al. | |
| 2016/0328517 | A1* | 11/2016 | Deng | G16H 30/40 |
| 2017/0091949 | A1 | 3/2017 | Akasaka et al. | |
| 2018/0240537 | A1 | 8/2018 | Sevenster et al. | |
| 2018/0314691 | A1* | 11/2018 | Mori | G06T 7/0012 |
| 2019/0362835 | A1* | 11/2019 | Sreenivasan | G06N 3/044 |
| 2021/0241884 | A1* | 8/2021 | Swisher | G06V 10/454 |

FOREIGN PATENT DOCUMENTS

| | | |
|---|---|---|
| JP | 2013039230 | 2/2013 |
| JP | 2013132514 | 7/2013 |
| JP | 2014096055 | 5/2014 |
| JP | 2017068380 | 4/2017 |
| JP | 2018509711 | 4/2018 |

OTHER PUBLICATIONS

Geoffrey D. Rubin et al., "Pulmonary Nodules on Multi-Detector Row CT Scans: Performance Comparison of Radiologists and Computer-aided Detection," Radiology, vol. 234, Jan. 2005, pp. 274-283.

"International Search Report (Form PCT/ISA/210) of PCT/JP2020/044239," mailed on Mar. 2, 2021, with English translation thereof, pp. 1-4.

"Written Opinion of the International Searching Authority (Form PCT/ISA/237)" of PCT/JP2020/044239, mailed on Mar. 2, 2021, with English translation thereof, pp. 1-7.

* cited by examiner

DOCUMENT CREATION SUPPORT APPARATUS, DOCUMENT CREATION SUPPORT METHOD, AND PROGRAM

CROSS-REFERENCE TO RELATED APPLICATION

This application is a continuation application of International Application No. PCT/JP2020/044239, filed Nov. 27, 2020, the disclosure of which is incorporated herein by reference in its entirety. Further, this application claims priority from Japanese Patent Application No. 2019-217420 filed on Nov. 29, 2019, the disclosures of which is incorporated herein by reference in its entirety.

BACKGROUND

1. Technical Field

Disclosed technologies relate to a document creation support apparatus, a document creation support method, and a program.

2. Description of the Related Art

In recent years, advances in medical devices, such as computed tomography (CT) apparatuses and magnetic resonance imaging (MRI) apparatuses, have enabled image diagnosis using high-resolution medical images with higher quality. In particular, a region of a lesion can be accurately specified by image diagnosis using CT images, MRI images, and the like, and appropriate treatment is being performed based on the specified result.

In addition, there is another image diagnosis method where medical images are analyzed by computer-aided diagnosis (CAD) to which a discriminator trained by a machine learning method such as deep learning is applied, regions, positions, volumes, and the like of lesions or the like included in the medical images are extracted, and the extracted ones are acquired as an analysis result (for example, "Pulmonary Nodules on Multi-Detector Row CT Scans: Performance Comparison of Radiologists and Computer-aided Detection"). In this way, the analysis result generated by the analysis process is saved in a database in association with examination information, such as a patient name, gender, age, and an imaging apparatus which has acquired a medical image, and is provided for diagnosis. In this case, a radiology technician or the like who has acquired a medical image determines a radiologist according to the medical image and informs the determined radiologist that the medical image and CAD analysis results are present. The radiologist interprets the medical image by referring to the distributed medical image and analysis result and creates an interpretation report, in his or her own interpretation terminal.

In addition, a method of generating findings from CAD analysis results by using a discriminator trained to output findings of a lesion size, shape, and presumed disease name, or the like by inputting the CAD analysis results has been proposed (see JP2013-39230A). Further, a method of generating an interpretation report including the findings presumed in this way based on a fixed form has also been proposed (see JP1995-31591A (JP-H7-31591A)). By automatically generating the interpretation report in this way, the burden on the radiologist in the case of creating the interpretation report can be reduced.

SUMMARY

For example, the automatic generation of an interpretation report based on a medical image is performed by the following procedure. First, by analyzing a medical image, a feature portion having an image feature such as an abnormal shadow included in the medical image is extracted. Next, a detailed analysis is performed on the feature portion to specify the properties of the feature portion. Next, a textual interpretation report is generated so that the specified properties can be understood.

According to the above-mentioned automatic generation method of an interpretation report, for example, in a case where a plurality of abnormal shadows are present in a medical image, a report is generated for each of the plurality of abnormal shadows. Then, as the interpretation report of the entire medical image, it is assumed that a plurality of reports generated for each abnormal shadow are presented in a list. Therefore, in a case where a large number of abnormal shadows are present in the medical image, the number of characters or the amount of information included in the interpretation report of the entire medical image becomes excessive, and the burden of checking the contents of the interpretation report becomes large.

The disclosed technology has been made in view of the above points, and an object thereof is to suppress an increase in the number of characters or the amount of information included in a text as the number of feature portions increases in the case of automatically generating the text including a description regarding the feature portions such as abnormal shadows included in an image to be diagnosed.

A document creation apparatus according to the disclosed technology is a document creation support apparatus comprising at least one processor. The processor is configured to generate a first text describing a property of a feature portion for each of a plurality of feature portions included in an image, classify the plurality of feature portions into at least one group, generate a second text integrating the first text generated for each of the feature portions belonging to the same group for each group, and generate a third text integrating the second text generated for each group.

The processor may perform control such that the first text generated for the feature portion belonging to a designated group is displayed according to the designation of any of the groups.

The processor may perform control such that in a case where a description regarding any of the groups in descriptions included in the third text is designated, the first text generated for the feature portion belonging to the designated group is displayed.

The processor may perform control such that in a case where any of the plurality of feature portions is designated, the first text generated for the designated feature portion and the first text generated for other feature portions belonging to the same group as the designated feature portion are displayed.

The processor may be configured to generate a common portion of each description of the first text generated for each of the feature portions belonging to the same group as the second text.

The processor may be configured to classify the plurality of feature portions based on a position where each of the plurality of feature portions is present.

The processor may be configured to classify the plurality of feature portions based on an area of an organ in which each of the plurality of feature portions is present.

The processor may be configured to acquire disease information indicating a disease corresponding to the feature portion for each of the plurality of feature portions, and classify the plurality of feature portions based on the disease information.

The processor may be configured to acquire property information indicating the property of the feature portion for each of the plurality of feature portions, and classify the plurality of feature portions based on the property information.

the processor may be configured to acquire the image, and extract the plurality of feature portions from the image.

A document creation support method according to the disclosed technology comprises: generating a first text describing a property of a feature portion for each of a plurality of feature portions included in an image; classifying the plurality of feature portions into at least one group; generating a second text integrating the first text generated for each of the feature portions belonging to the same group for each group; and generating a third text integrating the second text generated for each group.

A program according to the disclosed technology is a program for causing a computer to execute a process comprising: generating a first text describing a property of a feature portion for each of a plurality of feature portions included in an image; classifying the plurality of feature portions into at least one group; generating a second text integrating the first text generated for each of the feature portions belonging to the same group for each group; and generating a third text integrating the second text generated for each group.

According to the disclosed technology, it is possible to suppress an increase in the number of characters included in a text as the number of feature portions increases in the case of automatically generating the text including a description regarding the feature portions such as abnormal shadows included in an image to be diagnosed.

BRIEF DESCRIPTION OF THE DRAWINGS

Exemplary embodiments according to the technique of the present disclosure will be described in detail based on the following figures, wherein.

DETAILED DESCRIPTION

Figure 1:
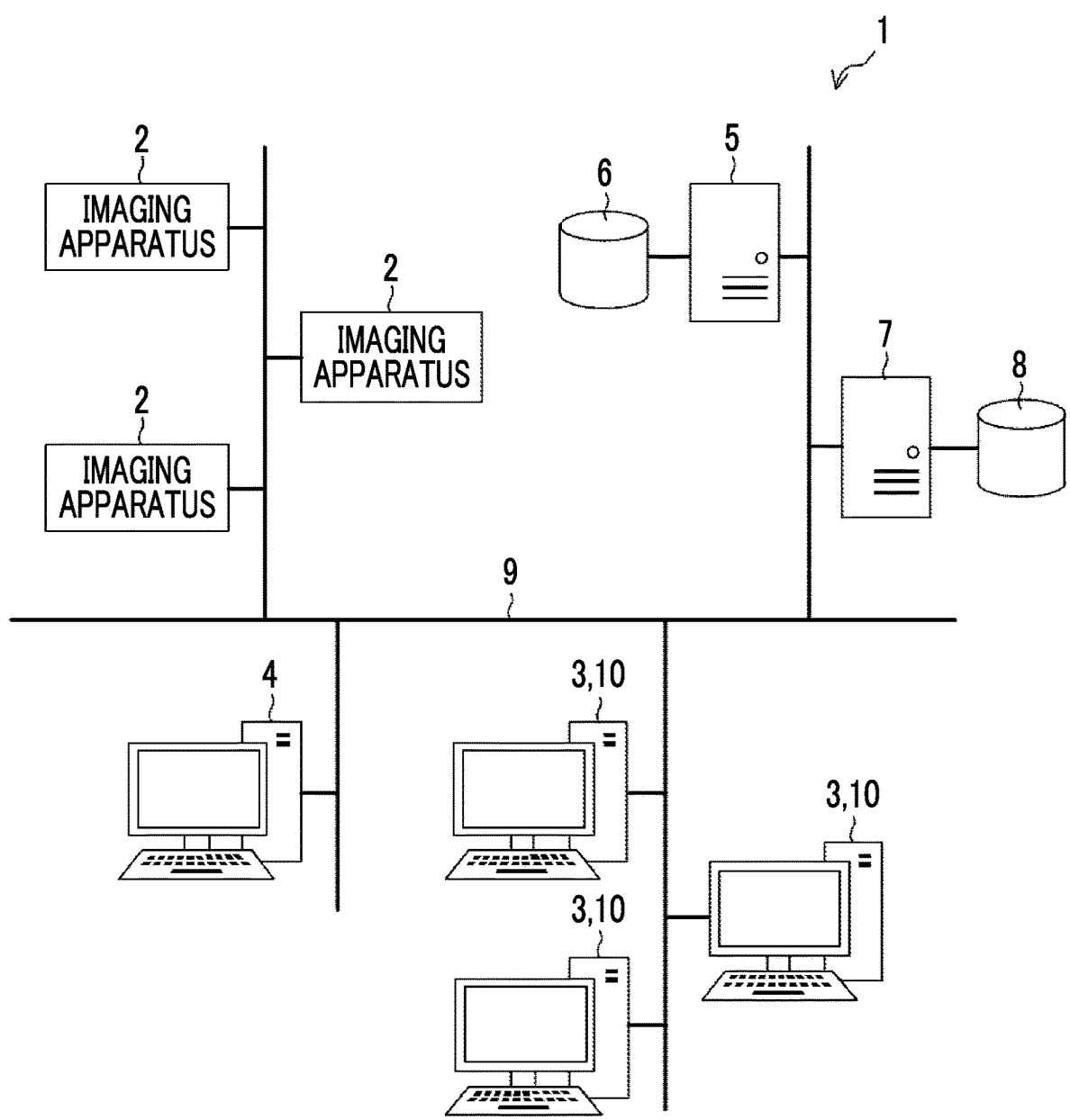
FIG. 1 is a diagram showing a schematic configuration of a medical information system according to an embodiment of the disclosed technology.

Hereinafter, embodiments of the disclosed technology will be described with reference to the drawings. In each drawing, substantially the same or equivalent components or portions are designated by the same reference numerals.

FIG. 1 is a diagram showing a schematic configuration of a medical information system 1 to which a document creation support apparatus according to an embodiment of the disclosed technology is applied. The medical information system 1 is, based on an examination order from a doctor in a medical department using a known ordering system, a system for imaging an examination target part of a subject, storing a medical image acquired by the imaging, interpreting the medical image by a radiologist and creating an interpretation report, and viewing the interpretation report and observing the medical image to be interpreted in detail by the doctor in the medical department that is a request source.

The medical information system 1 is configured to include a plurality of imaging apparatuses 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed on the computer from the recording medium. Alternatively, the application program is stored in a storage apparatus of a server computer connected to the network 9 or in a network storage in a state in which it can be accessed from the outside, and is downloaded to and installed on the computer in response to a request.

The imaging apparatus 2 is an apparatus that generates a medical image showing a diagnosis target part of the subject by imaging the diagnosis target part. The imaging apparatus 2 may be, for example, a simple X-ray imaging apparatus, a CT apparatus, an MRI apparatus, a positron emission tomography (PET) apparatus, and the like. A medical image generated by the imaging apparatus 2 is transmitted to the image server 5 and is saved therein.

The medical department WS 4 is a computer used by a doctor in a medical department to observe a medical image in detail, view an interpretation report, create an electronic medical record, and the like, and is configured to include a processing apparatus, a display apparatus such as a display, and an input apparatus such as a keyboard and a mouse. In the medical department WS 4, each process such as creating a medical record (electronic medical record) of a patient, requesting the image server 5 to view an image, displaying a medical image received from the image server 5, automatically detecting or highlighting suspected disease regions in the medical image, requesting the interpretation report server 7 to view an interpretation report, and displaying the interpretation report received from the interpretation report server 7 is performed by executing a software program for each process.

The image server 5 is a general-purpose computer on which a software program that provides a function of a database management system (DBMS) is installed. The image server 5 comprises the image database 6 including a storage. The image database 6 may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the imaging apparatus 2, the image server 5 prepares the medical image in a format for a database and registers the medical image in the image database 6.

Image data of the medical image acquired by the imaging apparatus 2 and accessory information attached to the image data are registered in the image database 6. The accessory information includes, for example, an image identification (ID) for identifying each medical image, a patient ID for identifying a patient who is a subject, an examination ID for identifying an examination content, a unique ID (UID: unique identification) allocated for each medical image, examination date and examination time at which a medical image is generated, the type of imaging apparatus used in an examination for acquiring a medical image, patient information such as the name, age, and gender of a patient, an examination part (imaging part), imaging information (an imaging protocol, an imaging sequence, an imaging method, imaging conditions, the presence or absence of the use of a contrast medium, and the like), and information such as a series number or a collection number when a plurality of medical images are acquired in one examination. In addition, in a case where a viewing request from the interpretation WS 3 is received through the network 9, the image server 5 searches for a medical image registered in the image database 6 and transmits the searched for medical image to the interpretation WS 3 that is a request source.

The interpretation report server 7 incorporates a software program for providing a function of a database management system to a general-purpose computer. In a case where the interpretation report server 7 receives a request to register an interpretation report from the interpretation WS 3, the interpretation report server 7 prepares the interpretation report in a format for a database and registers the interpretation report in the interpretation report database 8. Further, in a case where the request to search for the interpretation report is received, the interpretation report is searched from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings, and confidence of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the Internet or a dedicated line. In any case, it is preferable that the network 9 has a configuration capable of realizing high-speed transmission of medical images such as an optical network.

In the interpretation WS 3, each process such as requesting the image server 5 to view a medical image, various kinds of image processing on the medical image received from the image server 5, displaying the medical image, an analysis process on the medical image, highlighting the medical image based on the analysis result, creating the interpretation report based on the analysis result, supporting the creation of an interpretation report, requesting the interpretation report server 7 to register and view the interpretation report, and displaying the interpretation report received from the interpretation report server 7 is performed by executing a software program for each process. The interpretation WS 3 encompasses the document creation support apparatus 10 to be described later, and in the above processes, processes other than those performed by the document creation support apparatus 10 are performed by a well-known software program, and therefore the detailed description thereof will be omitted here. In addition, processes other than the processes performed by the document creation support apparatus 10 may not be performed in the interpretation WS 3, and a computer that performs the processes may be separately connected to the network 9, and in response to a processing request from the interpretation WS 3, the requested process may be performed by the computer. Hereinafter, the document creation support apparatus 10 encompassed in the interpretation WS 3 will be described in detail.

Figure 2:
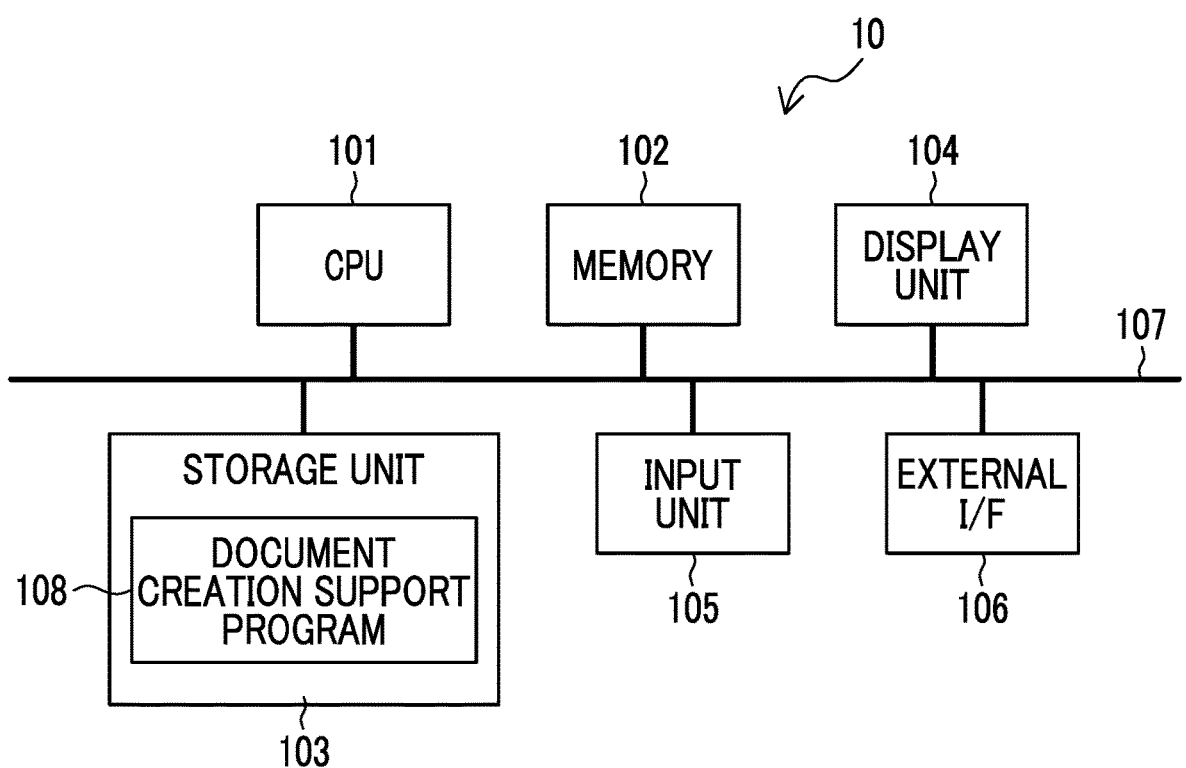
FIG. 2 is a diagram showing an example of a hardware configuration of a document creation support apparatus according to an embodiment of the disclosed technology.

FIG. 2 is a diagram showing an example of the hardware configuration of the document creation support apparatus 10. The document creation support apparatus 10 includes a central processing unit (CPU) 101, a memory 102, a storage unit 103, a display unit 104 such as a liquid crystal display, an input unit 105 such as a keyboard and a mouse, and an external interface (I/F) 106. The input unit 105 may be provided with a microphone that receives voice input. The CPU 101, the memory 102, the storage unit 103, the display unit 104, the input unit 105, and the external I/F 106 are connected to a bus 107. The document creation support apparatus 10 is connected to the network 9 of the medical information system 1 via the external I/F 106. The CPU 101 is an example of a processor in the disclosed technology.

The storage unit 103 is realized by a hard disk drive (HDD), a solid state drive (SSD), a flash memory, or the like. A document creation support program 108 is stored in the storage unit 103. The document creation support program 108 is recorded on a recording medium such as a DVD or a CD-ROM, distributed, and is installed on the document creation support apparatus 10 from the recording medium. Alternatively, the document creation support program 108 is stored in a storage apparatus of a server computer connected to the network or in a network storage in a state in which it can be accessed from the outside, and is downloaded to and installed on the document creation support apparatus 10 in response to a request. The CPU 101 reads the document creation support program 108 from the storage unit 103, loads the read document creation support program 108 into the memory 102, and executes the loaded document creation support program 108.

Figure 3:
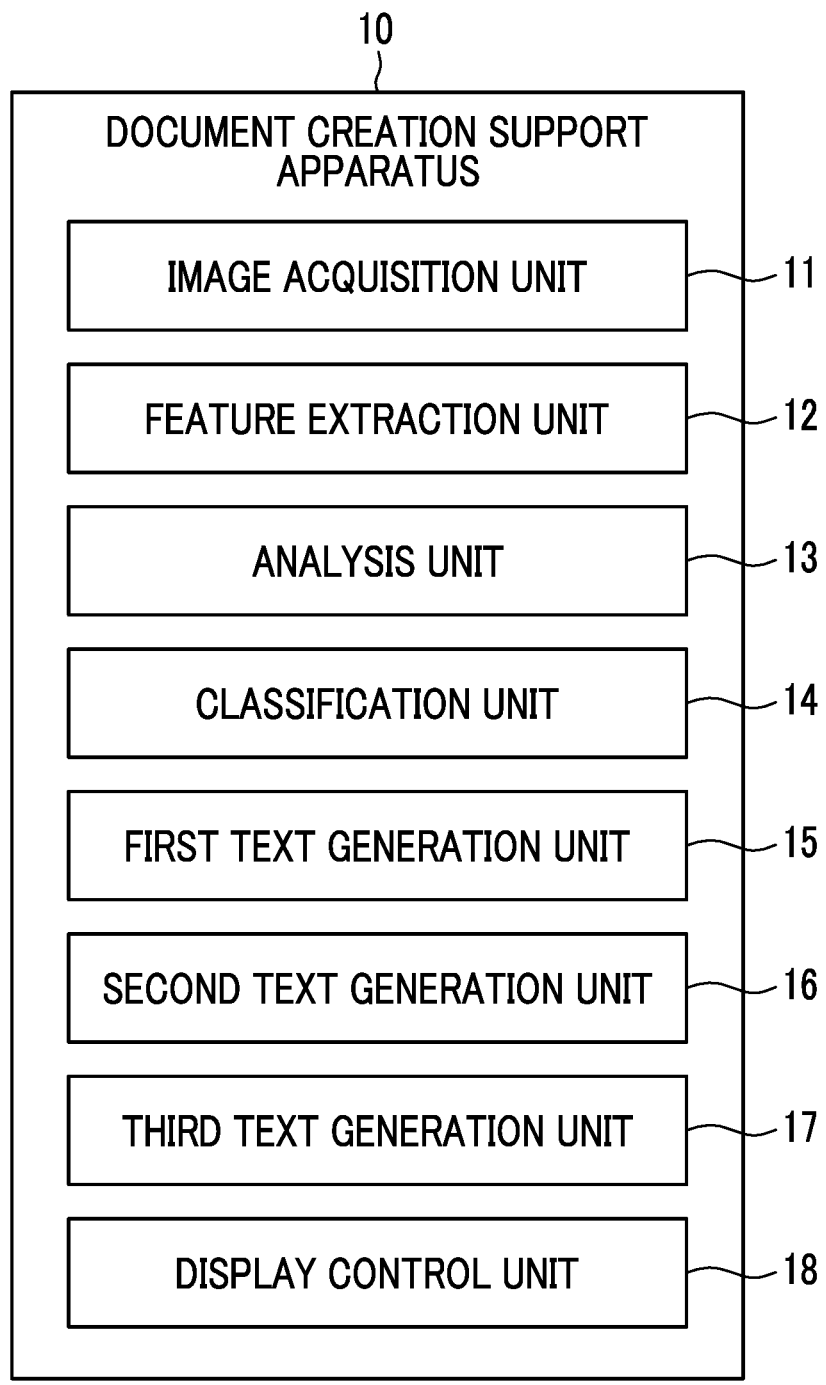
FIG. 3 is a functional block diagram showing an example of a functional configuration of the document creation support apparatus according to an embodiment of the disclosed technology.

FIG. 3 is a functional block diagram showing an example of the functional configuration of the document creation support apparatus 10. The document creation support apparatus 10 includes an image acquisition unit 11, a feature extraction unit 12, an analysis unit 13, a classification unit 14, a first text generation unit 15, a second text generation unit 16, a third text generation unit 17, and a display control unit 18. The CPU 101 executes the document creation support program 108, so that the document creation support apparatus 10 functions as the image acquisition unit 11, the feature extraction unit 12, the analysis unit 13, the classification unit 14, the first text generation unit 15, the second text generation unit 16, the third text generation unit 17, and the display control unit 18.

The image acquisition unit 11 acquires a medical image to be diagnosed (hereinafter referred to as a diagnosis target image). The diagnosis target image is saved in the image database 6, is transmitted from the image database 6 to the document creation support apparatus 10 in response to a request from the document creation support apparatus 10 (interpretation workstation 3), and is saved in the storage unit 103. The image acquisition unit 11 acquires the diagnosis target image saved in the storage unit 103. The image acquisition unit 11 may directly acquire the diagnosis target image saved in the image database 6 from the image database 6. In the following, a case where the diagnosis target image is a chest CT image will be described as an example.

Figure 4:
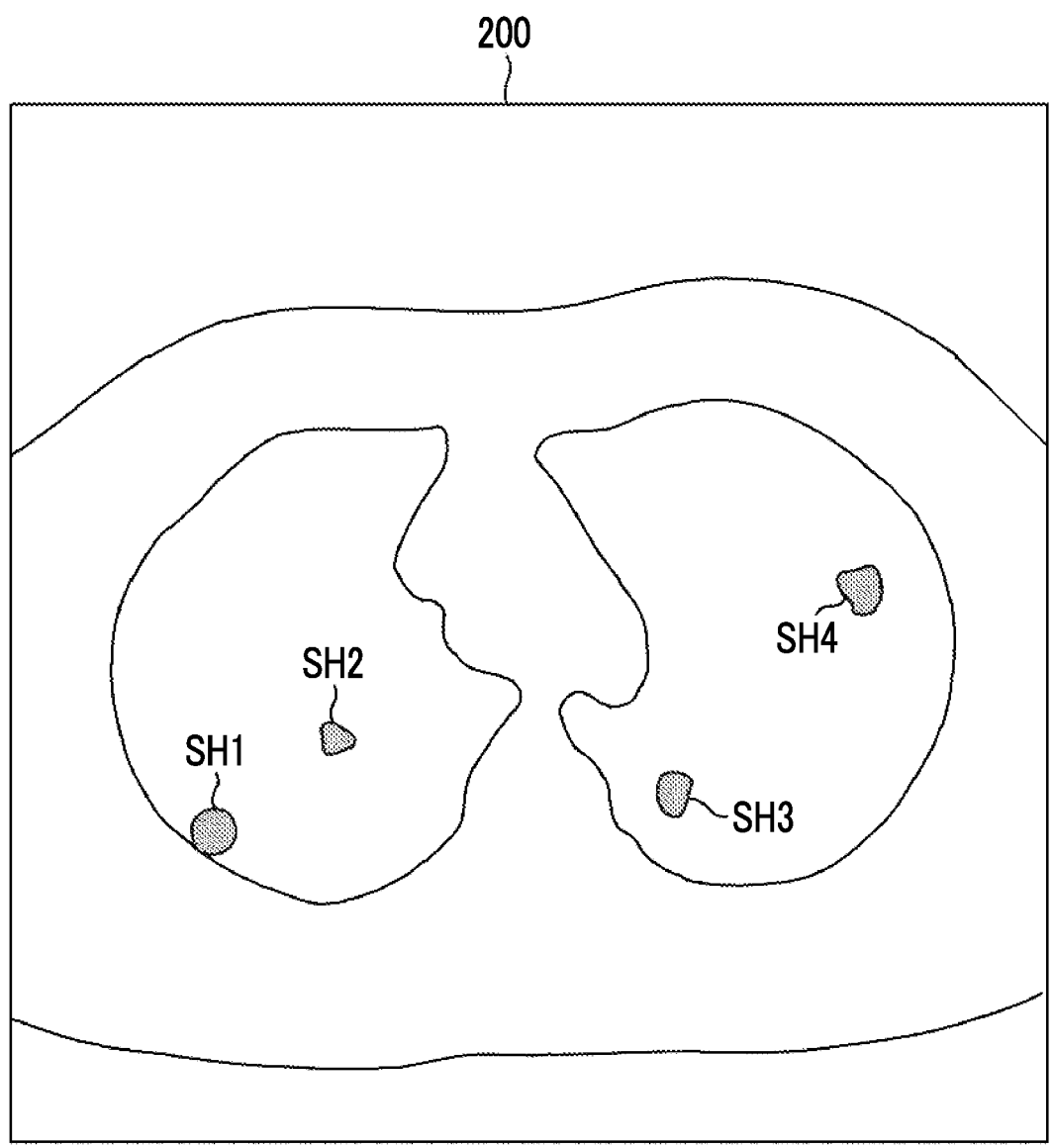
FIG. 4 is a diagram showing an abnormal shadow extracted from a diagnosis target image.

The feature extraction unit 12 extracts a shadow suspected of having a disease such as a nodule or pleural effusion (hereinafter referred to as an abnormal shadow) as a feature portion from the diagnosis target image acquired by the image acquisition unit 11. The feature extraction unit 12 may extract an abnormal shadow using, for example, a trained model learned by machine learning such as deep learning. The above-mentioned trained model is learned by machine learning using, for example, a plurality of combinations of a medical image including an abnormal shadow and information specifying a region in the image in which the abnormal shadow is present as training data. The above-mentioned trained model uses a medical image as an input and outputs a result of specifying an abnormal shadow region in the medical image. FIG. 4 shows an example in which an abnormal shadow [1] SH1, an abnormal shadow [2] SH2, an abnormal shadow [3] SH3, and an abnormal shadow [4] SH4 are extracted from a diagnosis target image 200.

The analysis unit 13 analyzes each of the abnormal shadows extracted by the feature extraction unit 12, and derives property information indicating the properties of the abnormal shadows. As an example of items of property information (hereinafter referred to as a property item), the position, size, transmittance (solid, frosted glass), the presence or absence of spicula, the presence or absence of calcification, the presence or absence of an irregular margin, the presence or absence of pleural invagination, the presence or absence of chest wall contact, the type of disease, and the like in the corresponding abnormal shadow can be mentioned. The analysis unit 13 may derive property information using, for example, a trained model learned by machine learning such as deep learning. The above-mentioned trained model is learned by machine learning using, for example, a plurality of combinations of a medical image including an abnormal shadow and a property label representing the property of the corresponding abnormal shadow as training data. The above-mentioned trained model uses a medical image as an input, and outputs a property score indicating the prominence of the property for each property item in the abnormal shadow included in the medical image. The analysis unit 13 derives the property information based on the above property score. For example, in a case where the property score for "transmittance", which is one of the property items, is 0.5 or more, the analysis unit 13 derives the property information indicating that the property regarding the transmittance of the corresponding abnormal shadow is "solid", and in a case where the property score is less than 0.5, the analysis unit 13 derives the property information indicating that the property regarding the transmittance of the corresponding abnormal shadow is "frosted glass". Further, in a case where the property score for "the presence or absence of spicula", which is one of the property items, is 0.5 or more, the analysis unit 13 derives the property information indicating that the property regarding the presence or absence of spicula of the corresponding abnormal shadow is "with spicula (positive)", and in a case where the property score is less than 0.5, the analysis unit 13 derives the property information indicating that the property regarding the presence or absence of spicula of the corresponding abnormal shadow is "no spicula (negative)". The threshold value 0.5 used for property determination is merely an example, and is set to an appropriate value for each property item.

Figure 5:
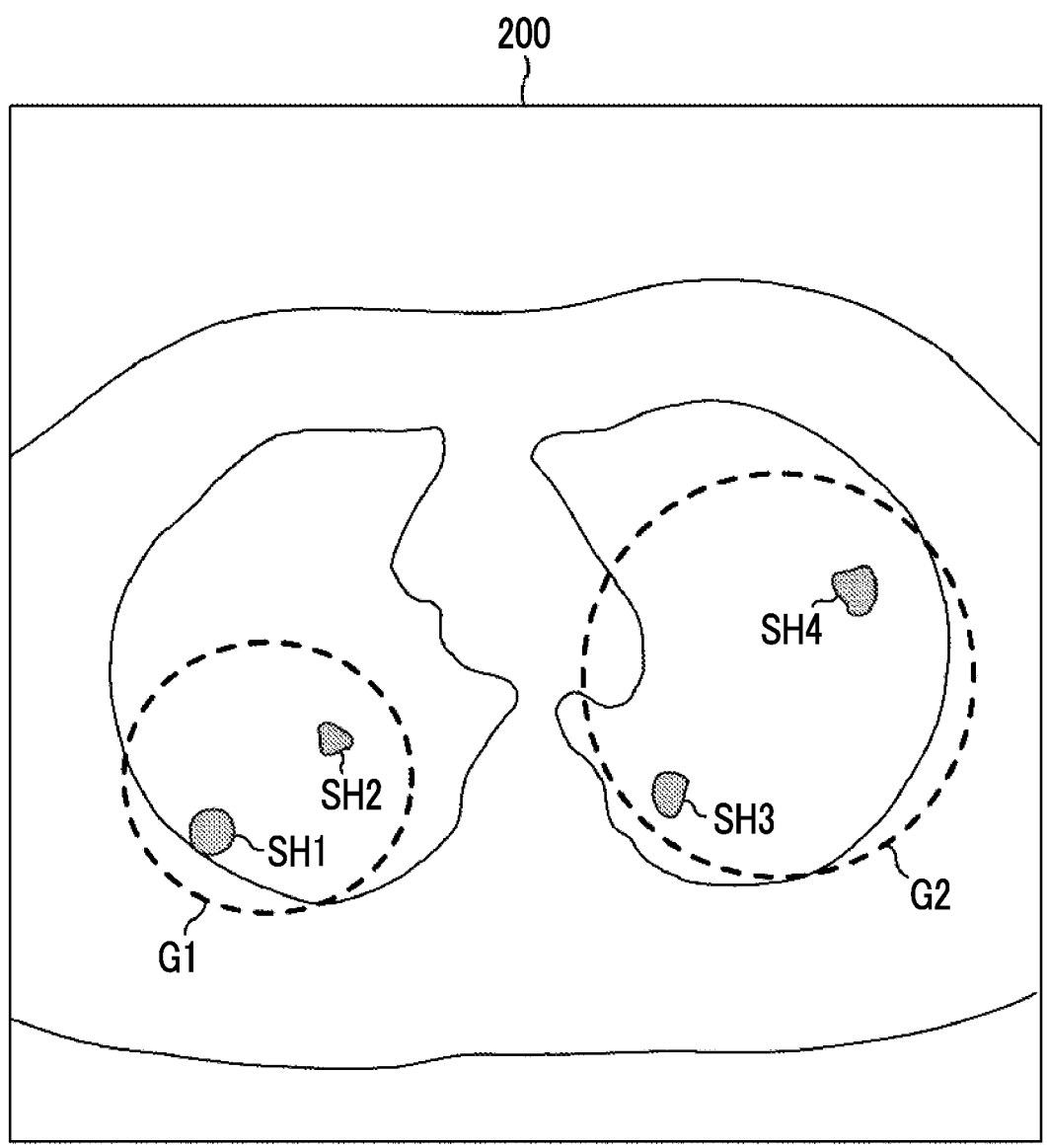
FIG. 5 is a diagram showing an example of a result of classifying abnormal shadows by a classification unit according to an embodiment of the disclosed technology.

The classification unit 14 classifies the abnormal shadows extracted by the feature extraction unit 12 into at least one group. That is, the classification unit 14 groups the extracted abnormal shadows. In the present embodiment, the classification unit 14 specifies a position where each of the extracted abnormal shadows is present, and classifies a feature portion based on the specified position. In this case, the classification unit 14 may specify an area of the organ in which each of the abnormal shadows is present, and classify the abnormal shadows based on the specified area. For example, classification may be performed according to whether the abnormal shadow is present in the left or right lung. In addition, classification may be performed according to where the abnormal shadow is present in the five lobes (left upper lobe, left lower lobe, right upper lobe, right middle lobe, and right lower lobe). Further, classification may be performed according to where the abnormal shadow is present in the predetermined lung area for each of the right lung and the left lung. FIG. 5 shows an example in which the classification unit 14 classifies the abnormal shadow [1] SH1 and the abnormal shadow [2] SH2 present in the right lung into a group [1] G1 and classifies the abnormal shadow [3] SH3 and the abnormal shadow [4] SH4 present in the left lung into a group [2] G2. As the information regarding the position where the abnormal shadow is present, it is also possible to use the property information derived by the analysis unit 13.

Figure 6:
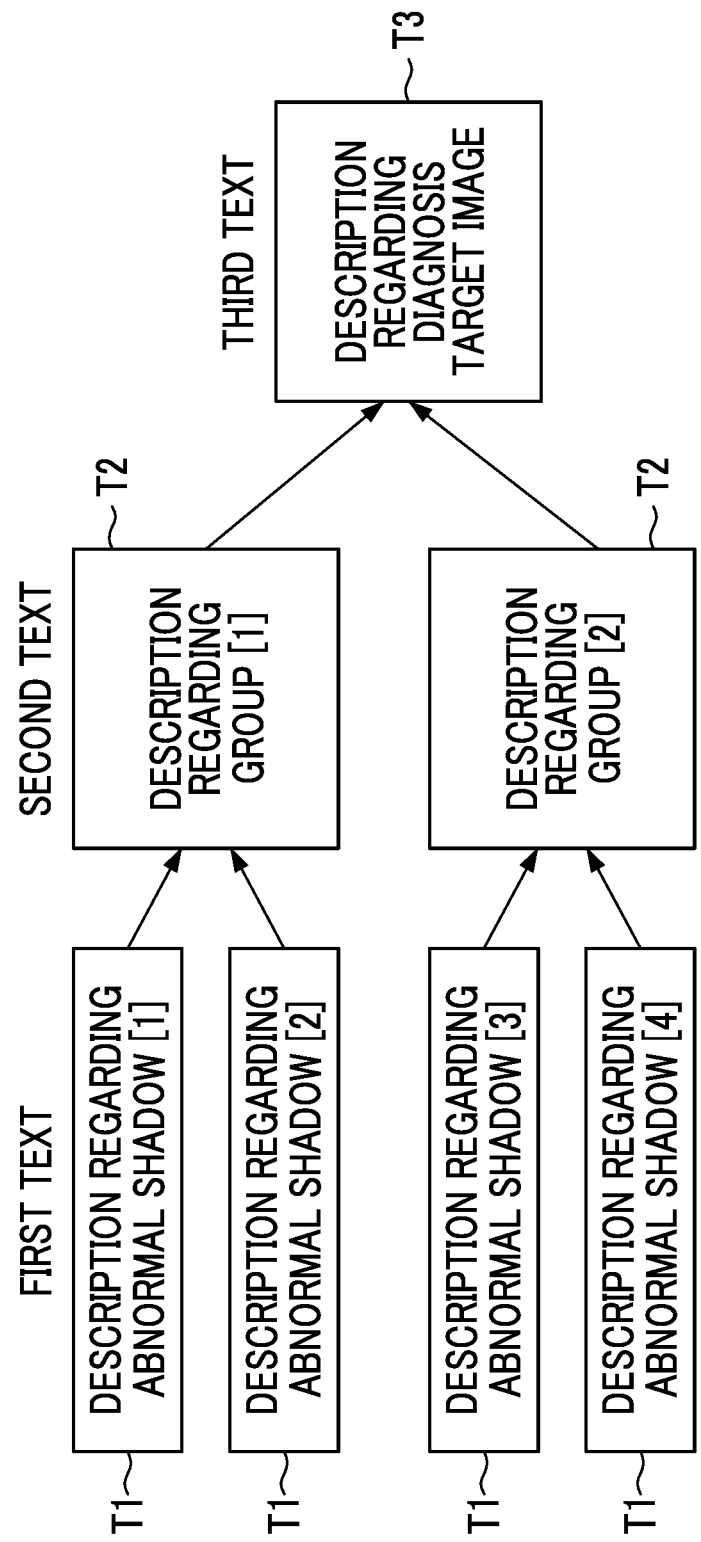
FIG. 6 is a diagram showing an example of first to third texts generated by first to third text generation units according to an embodiment of the disclosed technology.

The first text generation unit 15 generates first texts (interpretation report) describing the properties of an abnormal shadow for each of the abnormal shadows extracted by the feature extraction unit 12. The first text generation unit 15 saves each of the generated first texts in the storage unit 103. The first text generation unit 15 generates the first text based on the property information derived by the analysis unit 13. FIG. 6 shows an example in which the first text generation unit 15 generates a first text T1 for each of the abnormal shadow [1] SH1, the abnormal shadow [2] SH2, the abnormal shadow [3] SH3, and the abnormal shadow SH4 for the diagnosis target image 200 shown in FIG. 4.

Figure 7:
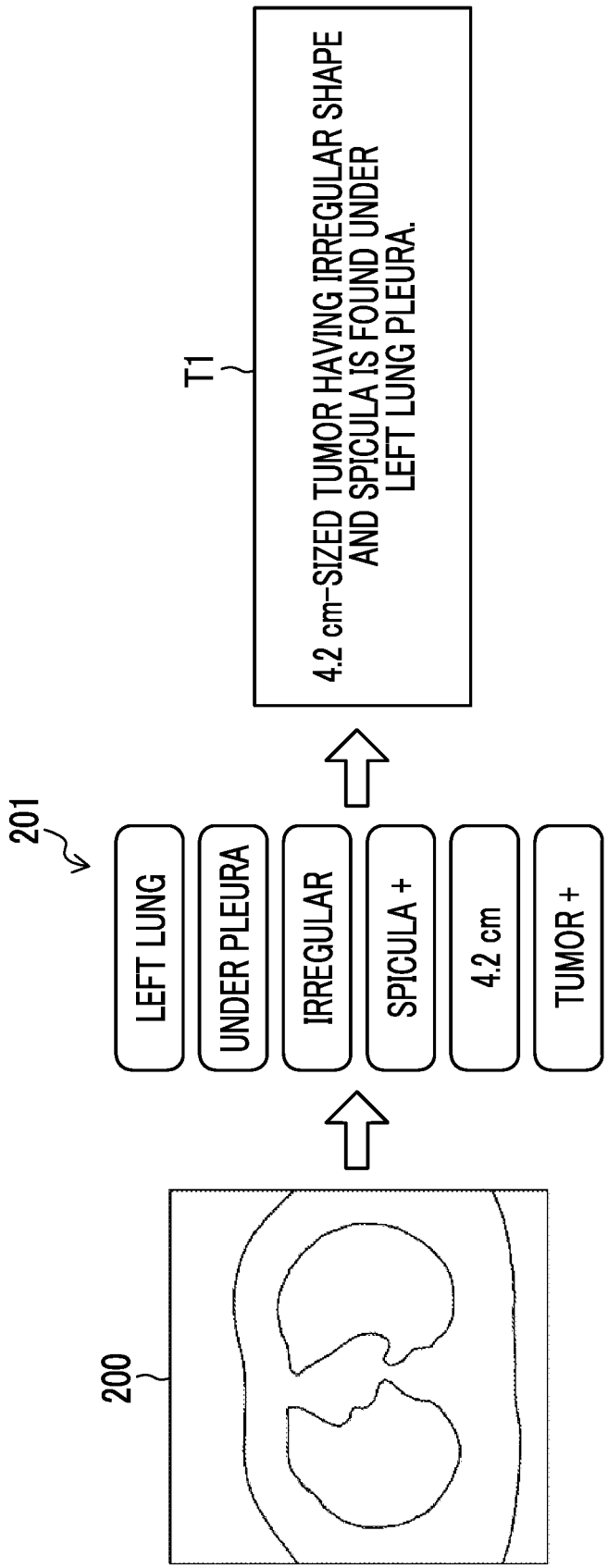
FIG. 7 is a diagram showing an example of an analysis result by an analysis unit and a first text generated by the first text generation unit according to an embodiment of the disclosed technology.

FIG. 7 shows an example in which the analysis unit 13 analyzes abnormal shadows included in the diagnosis target image 200, and derives "left lung", "under pleura", "irregular", "spicula +", "4.2 cm", and "tumor +" as property information 201 of the corresponding abnormal shadow, and the first text generation unit 15 generates a text "A 4.2 cm-sized tumor having an irregular shape and spicula is found under the left lung pleura." for the corresponding abnormal shadow as the first text T1 based on the property information 201. The "+" notation in the property information 201 indicates that the property is positive.

Figure 8:
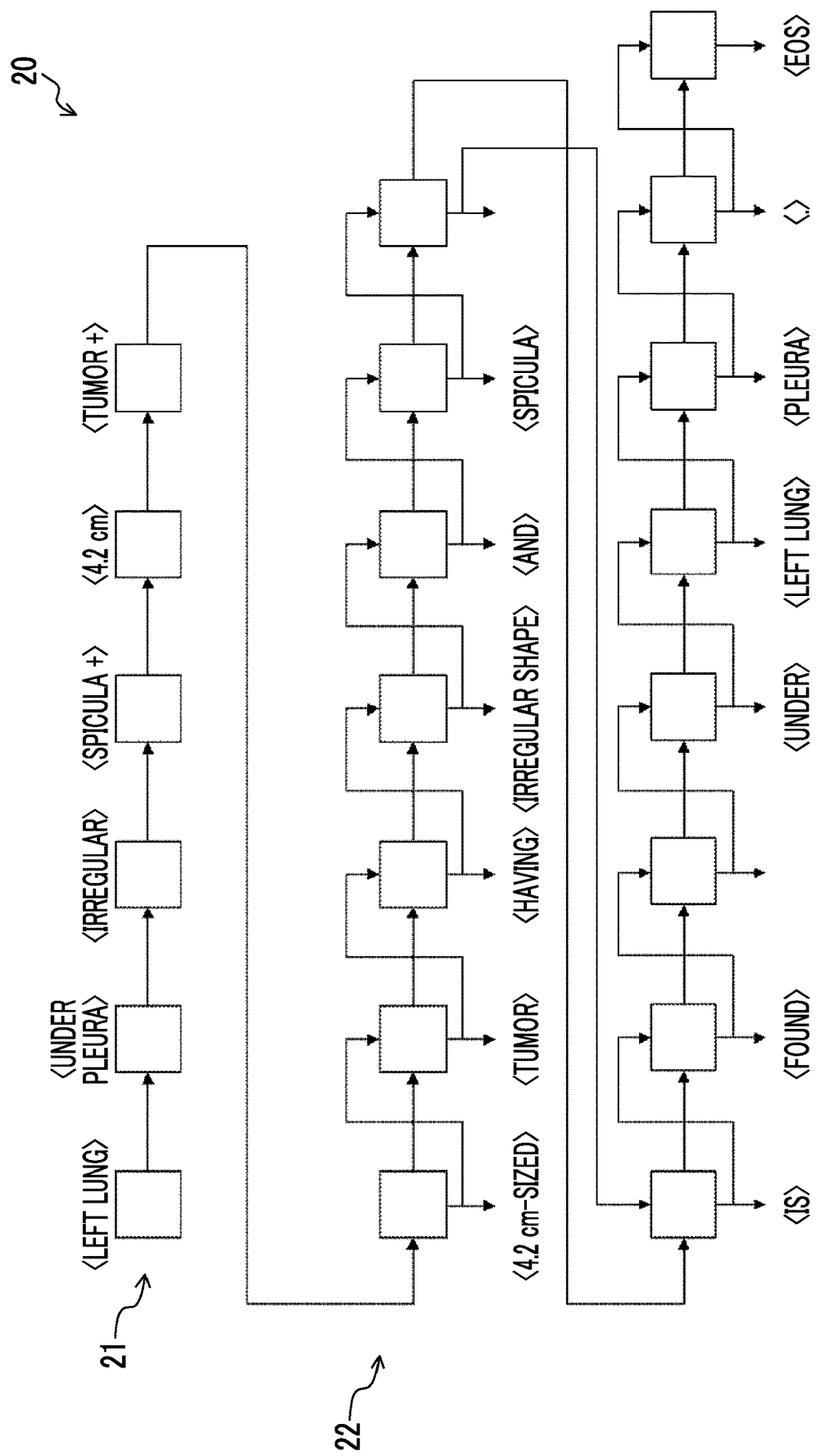
FIG. 8 is a diagram schematically showing an example of a configuration of a recurrent neural network constituting the first text generation unit according to an embodiment of the disclosed technology.

The first text generation unit 15 includes a recurrent neural network trained to create a text from the input words. FIG. 8 is a diagram schematically showing a configuration of a recurrent neural network. As shown in FIG. 8, the recurrent neural network 20 includes an encoder 21 and a decoder 22. Characters corresponding to the property information derived by the analysis unit 13 are input to the encoder 21. For example, "left lung", "under pleura", "irregular", "spicula +", "4.2 cm", and "tumor +" in which the property information derived by the analysis unit 13 is transcribed are input to the encoder 21. The decoder 22 has been learned to document the words input to the encoder 21, and from the above input words, the text "A 4.2 cm-sized tumor having an irregular shape and spicula is found under the left lung pleura." is generated. In FIG. 8, "EOS" indicates the end of the sentence (End Of Sentence).

The second text generation unit 16 generates second texts integrating the first texts generated for each of the abnormal shadows belonging to the same group, for each group classified by the classification unit 14. The second text generation unit 16 saves each of the generated second texts in the storage unit 103. FIG. 6 shows an example in which the second text generation unit 16 generates a second text T2 integrating the first texts T1 generated for each of the abnormal shadow [1] SH1 and the abnormal shadow [2] SH2 belonging to the group [1] G1 and generates a second text T2 integrating the first texts T1 generated for each of the abnormal shadow [3] SH3 and the abnormal shadow [4] SH4 belonging to the group [2] G2.

The second text generation unit 16 may generate, for example, a common (overlapping) portion of each description of the first texts generated for each of the abnormal shadows belonging to the same group as the second text. That is, the non-common (non-overlapping) portion of each description of the first texts generated for each of the abnormal shadows belonging to one group is not included in the second text. Thereby, the second text T2 describes the information regarding the properties of each of the abnormal shadows belonging to the same group in a summarized state.

For example, it is assumed that the first text generated for the abnormal shadow [1] SH1 belonging to group [1] G1 is "A 3 cm-sized solid nodule is found in the left lung. It is accompanied by spicula and has an irregular margin.", and the first text generated for the other abnormal shadow [2] SH2 belonging to group [1] G1 is "A 1 cm-sized solid nodule is found in the left lung. It has an irregular margin and is accompanied by a cavity in the center." In this case, the second text generation unit extracts the common portions ("left lung", "irregular margin", "solid", and "nodule") of these descriptions and generates a second text such as "A plurality of solid nodules with irregular margins are found in the left lung."

In this case, the second text generation unit 16 may use, for example, a trained model learned by machine learning such as deep learning, and generate a common portion of each description of the plurality of first texts as the second text. The above-mentioned trained model is learned by machine learning using, for example, a plurality of combinations of a plurality of texts and one text in which the plurality of texts are integrated as training data. The above-mentioned trained model uses a plurality of texts as inputs, and outputs one text describing the common portions of the plurality of texts.

Further, the second text generation unit 16 may compare, for example, the property information of each abnormal shadow belonging to the same group derived by the analysis unit 13, and output the text generated based on the common property information (in the case of the above example sentence, "left lung", "irregular margin", "solid +", and "nodule +" are assumed) as the second text. In this case, the second text generation unit 16 may include a recurrent neural network similar to the first text generation unit 15.

In addition, instead of generating the common (overlapping) portion of each description of the first texts generated for each abnormal shadow as the second text, the second text generation unit 16 may generate, as the second text, a text obtained by extracting only the description regarding the property item selected based on a predetermined priority from each description of the first text. For example, the second text generation unit 16 may generate, as a second text regarding the group [1] G1, a combination of a description of the property item selected based on the priority from the descriptions of the first text generated for the abnormal shadow [1] SH1 and a description of the property item selected based on the priority from the descriptions of the first text generated for the abnormal shadow [2] SH2.

The third text generation unit 17 generates a third text integrating the second texts generated for each group. The third text generation unit 17 saves the generated third text in the storage unit 103. FIG. 6 shows an example in which the third text generation unit 17 generates a third text T3 integrating the second texts T2 generated for each of the group [1] G1 and the group [2] G2.

The third text generation unit 17 may generate, for example, a simple combination of the second texts generated for each group as the third text. Further, the third text generation unit 17 may generate a common (overlapping) portion of each description of the second texts generated for each group as the third text. That is, in this case, the non-common (non-overlapping) portion of each description of the second texts generated for each group is not included in the third text.

The display control unit 18 allocates a display region for displaying the description regarding each group included in the third text on the display screen of the display unit 104 for each group. The display control unit 18 embeds information in each of the display regions of each group, which enables access to each of the first texts generated for each abnormal shadow belonging to the group.

For example, the display control unit 18 embeds a hyperlink in the display region corresponding to the description regarding the group [1] G1 included in the third text, which enables access to the first texts generated for each of the abnormal shadow [1] SH1 and the abnormal shadow [2] SH2 belonging to the group [1] G1. Similarly, the display control unit 18 embeds a hyperlink in the display region corresponding to the description regarding the group [2] G2 included in the third text, which enables access to the first texts T1 generated for each of the abnormal shadow [3] SH3 and the abnormal shadow [4] SH4 belonging to the group [2] G2.

Further, the display control unit 18 embeds information in an image region of each of the abnormal shadows extracted from the diagnosis target image by the feature extraction unit 12, which enables access to the first text generated for the corresponding abnormal shadow and the first texts generated for other abnormal shadows belonging to the same group as the corresponding abnormal shadow. For example, the display control unit 18 embeds information in an image region of the abnormal shadow [1] SH1, which enables access to the first text generated for the abnormal shadow [1] SH1 and the first text generated for the abnormal shadow [2] SH2 belonging to the same group as the abnormal shadow [1] SH1.

Similarly, the display control unit 18 embeds hyperlink information in an image region of the abnormal shadow [2] SH2, which enables access to the first text generated for the abnormal shadow [2] SH2 and the first text generated for the abnormal shadow [1] SH1 belonging to the same group as the abnormal shadow [2] SH2. Similarly, the display control unit 18 embeds information in an image region of the abnormal shadow [3] SH3, which enables access to the first text generated for the abnormal shadow [3] SH3 and the first text generated for the abnormal shadow [4] SH4 belonging to the same group as the abnormal shadow [3] SH3. Similarly, the display control unit 18 embeds information in an image region of the abnormal shadow [4] SH4, which enables access to the first text generated for the abnormal shadow [4] SH4 and the first text generated for the abnormal shadow [3] SH3 belonging to the same group as the abnormal shadow [4] SH4.

Figure 9:
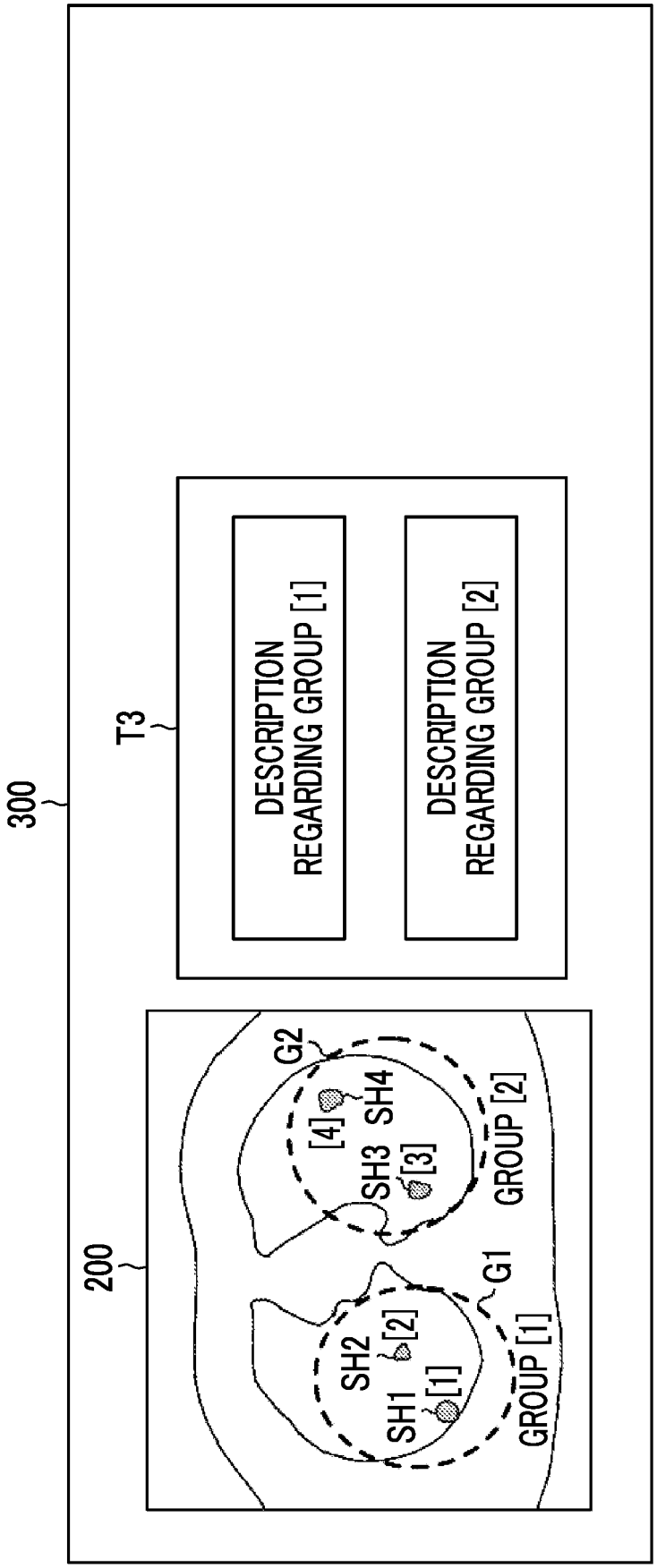
FIG. 9 is a diagram showing an example of a display mode on a display screen according to an embodiment of the disclosed technology.

Further, as illustrated in FIG. 9, the display control unit 18 performs control such that the diagnosis target image 200 and the third text T3 generated for the diagnosis target image 200 are displayed on a display screen 300 of the display unit 104. At this time, as illustrated in FIG. 9, the display control unit 18 may perform control such that the identification codes [1] to [4] for identifying a plurality of abnormal shadows are displayed in the vicinity of the corresponding abnormal shadows in the display region of the diagnosis target image 200. Further, as illustrated in FIG. 9, the display control unit 18 may perform control such that information indicating the classification result of the abnormal shadows by the classification unit 14 is displayed.

The display control unit 18 performs control such that each of the first texts generated for each of the abnormal shadows belonging to a designated group is displayed on the display screen 300 according to the designation of any of the groups set for each abnormal shadow.

Figure 10:
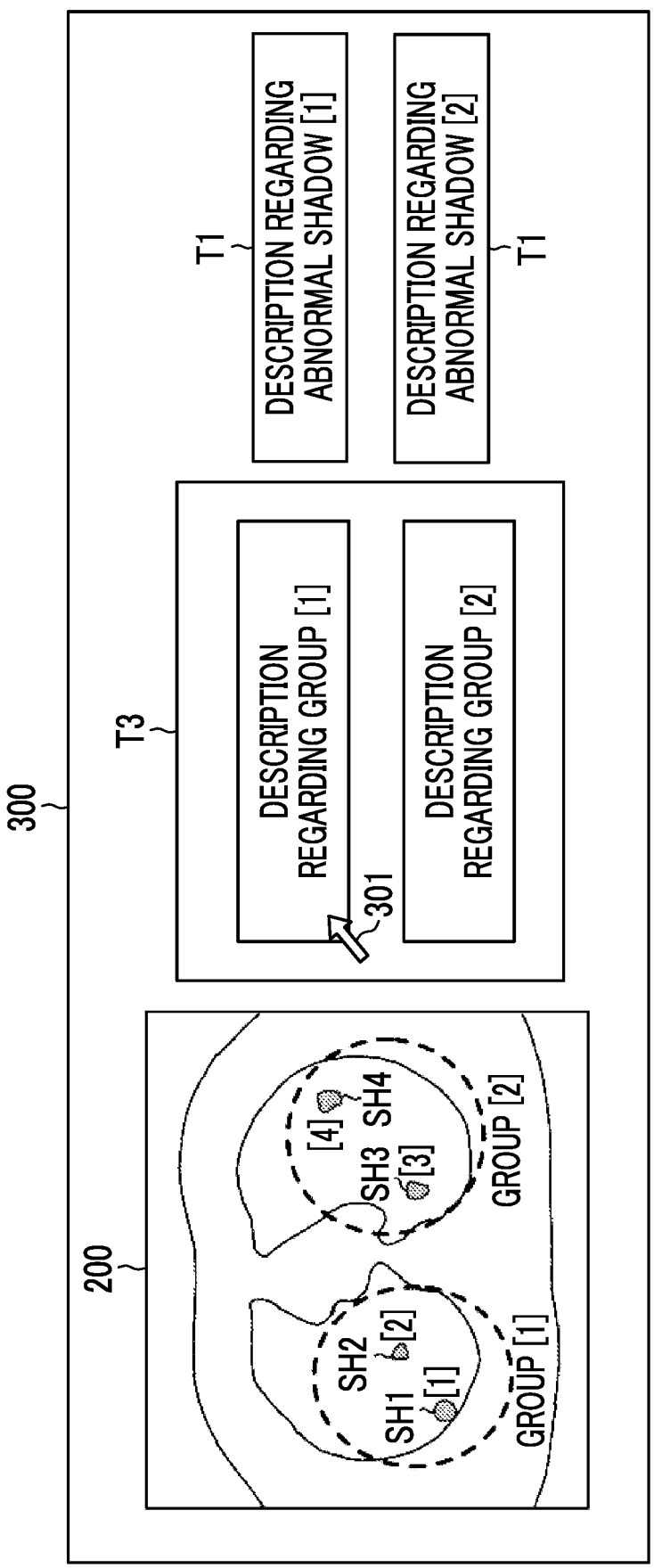
FIG. 10 is a diagram showing an example of a display mode on the display screen according to an embodiment of the disclosed technology.

For example, as shown in FIG. 10, in a case where the display region of the description regarding the group [1] G1 included in the third text T3 displayed on the display screen 300 is designated by using the pointer 301, the display control unit 18 performs control based on hyperlinks embedded in the designated display region such that the first texts T1 generated for each of the abnormal shadow [1] SH1 and the abnormal shadow [2] SH2 belonging to the group [1] G1 are read from the storage unit 103, and these texts are displayed on the display screen 300.

Figure 11:
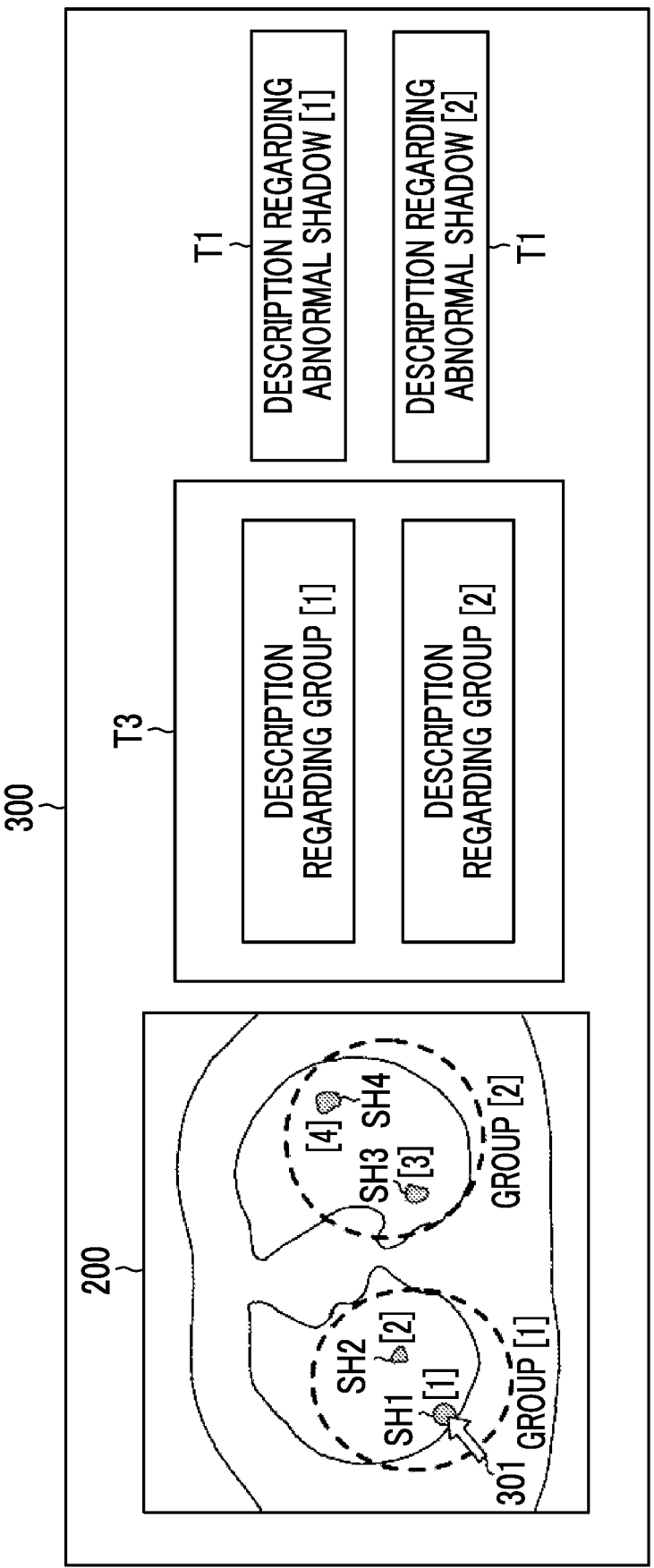
FIG. 11 is a diagram showing an example of a display mode on the display screen according to an embodiment of the disclosed technology.

Further, for example, as shown in FIG. 11, in a case where the image region of the abnormal shadow [1] SH1 of the diagnosis target image 200 displayed on the display screen 300 is designated by using the pointer 301, the display control unit 18 performs control based on hyperlinks embedded in the designated image region such that the first text T1 generated for the abnormal shadow [1] SH1 and the first text T1 generated for the abnormal shadow [2] SH2 belonging to the same group [1] G1 as the abnormal shadow [1] SH1 are read from the storage unit 103, and these texts are displayed on the display screen 300.

Figure 12:
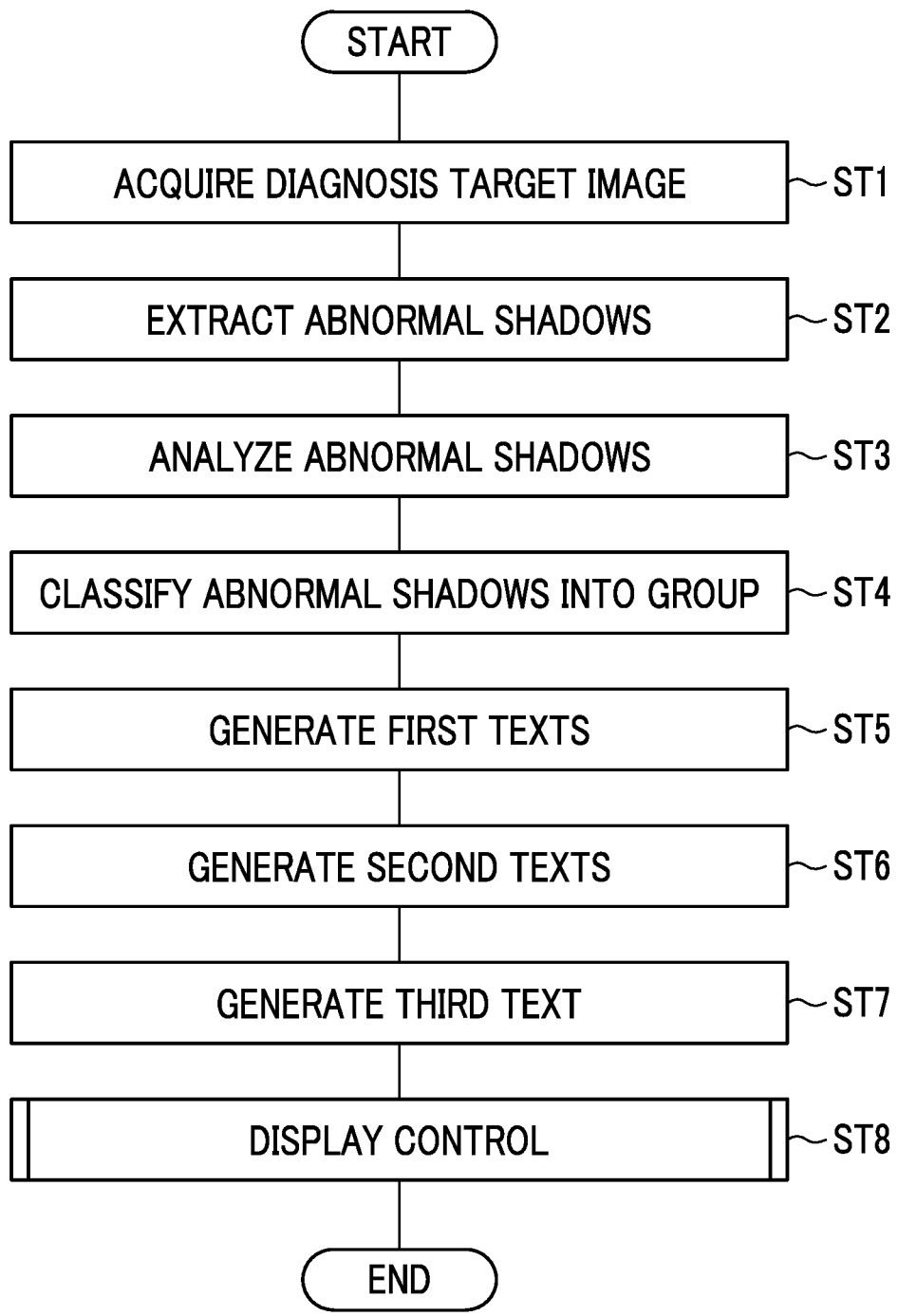
FIG. 12 is a flowchart showing an example of a flow of a document creation support process according to an embodiment of the disclosed technology.

In the following, the operation of the document creation support apparatus 10 will be described. FIG. 12 is a flowchart showing an example of a flow of a document creation support process performed by the CPU 101 executing the document creation support program 108. The document creation support program 108 is executed, for example, in a case where an instruction to start execution is input by a user via the input unit 105. It is assumed that diagnosis target image is downloaded from the image server 5 to the document creation support apparatus 10 (interpretation workstation 3) and is saved in the storage unit 103.

In Step ST1, the image acquisition unit 11 acquires the diagnosis target image saved in the storage unit 103. In Step ST2, the feature extraction unit 12 extracts abnormal shadows as feature portions from the diagnosis target image acquired by the image acquisition unit 11. In Step ST3, the analysis unit 13 analyzes each of the abnormal shadows extracted from the diagnosis target image, and derives property information indicating the properties of the abnormal shadows. In Step ST4, the classification unit 14 classifies the extracted abnormal shadows into at least one group. In the present embodiment, the classification unit 14 classifies the abnormal shadows based on the position where each abnormal shadow is present.

In Step ST5, the first text generation unit 15 generates first texts describing the properties of the corresponding abnormal shadow each of the abnormal shadows extracted from the diagnosis target image. The first text generation unit 15 saves each of the generated first texts in the storage unit 103. In Step ST6, the second text generation unit 16 generates second texts T2 integrating the first texts generated for each of the abnormal shadows belonging to the same group, for each group. The second text generation unit 16 saves each of the generated second texts in the storage unit 103. In Step ST7, the third text generation unit 17 generates a third text integrating the second texts generated for each group. The third text generation unit 17 saves the generated third text in the storage unit 103.

Figure 13:
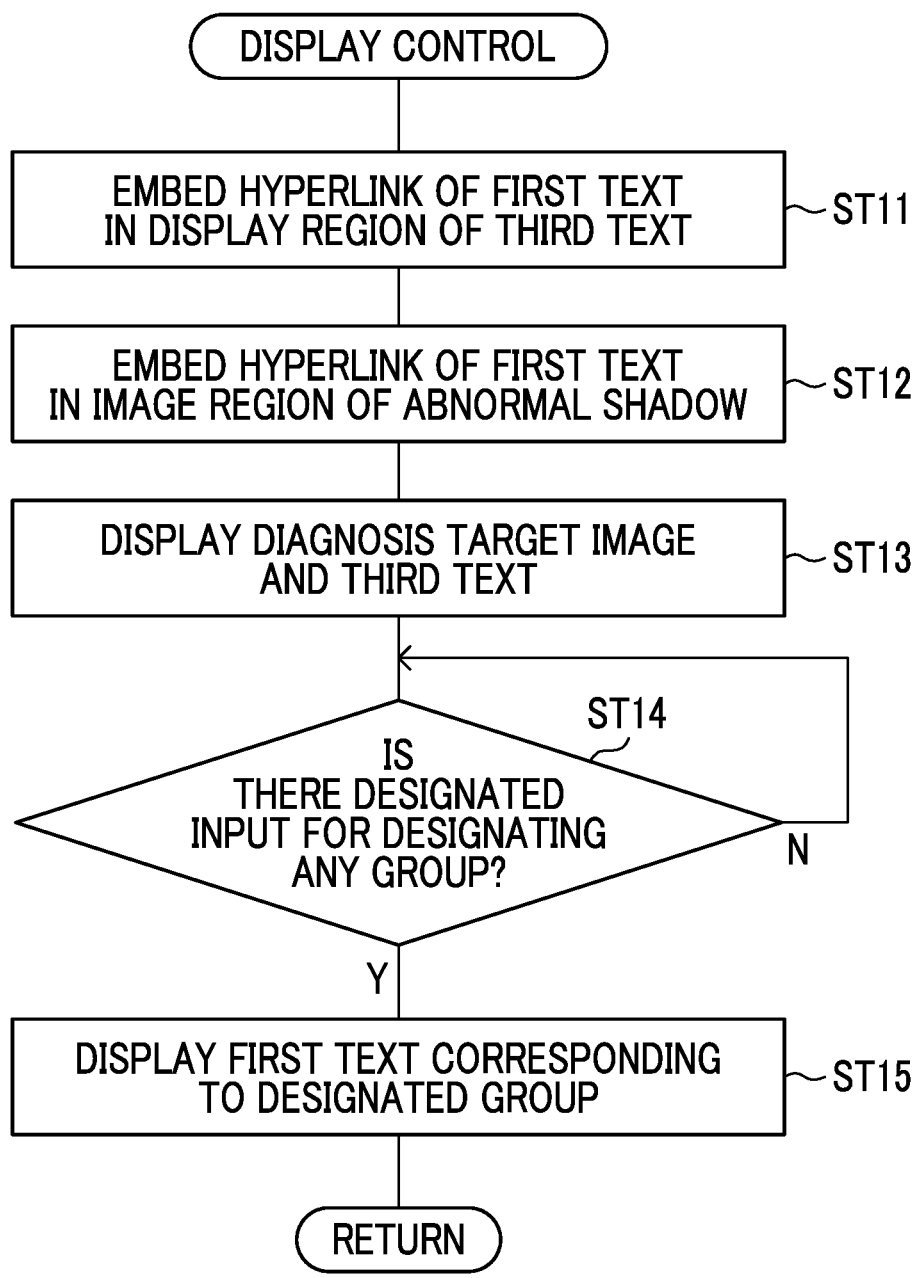
FIG. 13 is a flowchart showing an example of a flow of a display control process according to an embodiment of the disclosed technology.

In Step ST8, the display control unit 18 controls the display on the display unit 104. FIG. 13 is a flowchart showing details of display control in the display control unit 18.

In Step ST11, the display control unit 18 allocates a display region for displaying the description regarding each group included in the third text on the display screen of the display unit 104, for each group. The display control unit 18 embeds information (hyperlink) in each of the display regions of each group, which enables access to each of the first texts generated for each abnormal shadow belonging to the group.

In Step ST12, the display control unit 18 embeds information (hyperlink) in an image region of each of the abnormal shadows extracted from the diagnosis target image, which enables access to the first text generated for the corresponding abnormal shadow and the first texts generated for other abnormal shadows belonging to the same group as the corresponding abnormal shadow.

In Step ST13, as illustrated in FIG. 9, the display control unit 18 performs control such that the diagnosis target image 200 and the third text T3 generated for the diagnosis target image 200 are displayed on the display screen 300 of the display unit 104.

In Step ST14, the display control unit 18 determines whether or not there is a designated input for designating any group with respect to the diagnosis target image 200 or the third text T3 displayed on the display screen 300 of the display unit 104. For example, the designated input for designating a group can be performed by designating, as illustrated in FIG. 10, the display region for each group in the description of the third text T3 with the pointer 301, or by designating, as illustrated in FIG. 11, the image region of the abnormal shadow included in the diagnosis target image 200 with the pointer 301.

In a case where the display control unit 18 determines that there is a designated input for designating a group, in Step ST15, as illustrated in FIGS. 10 and 11, the display control unit 18 performs control such that the first text T1 generated for each abnormal shadow belonging to the designated group is displayed on the display screen 300 of the display unit 104.

As described above, with the document creation support apparatus 10 according to the embodiment of the disclosed technology, the first text generation unit 15 generates a first text describing the properties of each abnormal shadow extracted from the diagnosis target image. The second text generation unit 16 generates second texts integrating the first texts generated for each of feature portions belonging to the same group, for each group. The third text generation unit 17 generates a third text integrating the second texts generated for each group. That is, the third text is described in a state where the information regarding the properties of each abnormal shadow extracted from the diagnosis target image is summarized.

Therefore, it is possible to suppress the number of characters or the amount of information included in the text as compared with the case where the first texts generated for each abnormal shadow are simply presented in a list. That is, it is possible to suppress an increase in the number of characters or the amount of information included in the text as the number of abnormal shadows increases. This makes it possible to reduce the burden of checking the content of the text.

Further, according to the document creation support apparatus 10, the first text generated for each of the abnormal shadows belonging to the designated group is displayed on the display screen according to the designated input for designating any of the groups. This makes it possible for a user who has checked the content of the third text presented as a summarized interpretation report to provide desired information in a case where he/she desires to acquire more detailed information about a specific abnormal shadow.

In the above embodiment, the case where the classification unit 14 classifies the plurality of abnormal shadows based on the position where each of the plurality of abnormal shadows is present has been exemplified, but the present disclosure is not limited to this embodiment. For example, the classification unit 14 may acquire disease information indicating what kind of disease each abnormal shadow corresponds to for each of a plurality of abnormal shadows, and classify the plurality of abnormal shadows based on the disease information. In this case, the classification unit 14 may classify a plurality of abnormal shadows by using the disease group information that specifies the diseases that are classified into the same group.

For example, nodules, lymphadenopathy, and pleural effusion are diseases that originate from cancer, respectively, and in the disease group information, these diseases are specified as diseases classified into the same group. Further, the classification unit 14 specifies that the disease corresponding to the abnormal shadow [1] SH1 is a nodule and the disease corresponding to the abnormal shadow [2] SH2 is lymphadenopathy based on the disease information. In this case, the classification unit 14 classifies the abnormal shadow [1] SH1 and the abnormal shadow [2] SH2 so that they belong to the same group based on the disease information and the disease group information. It is also possible to use the information indicating the type of the disease included in the property information derived by the analysis unit 13 analyzing the abnormal shadow as the disease information.

Further, the classification unit 14 may acquire the property information derived by the analysis unit 13 and classify a plurality of abnormal shadows based on the acquired property information. In this case, the classification unit 14 may classify a plurality of abnormal shadows by using the property group information that specifies the properties that are classified into the same group for each group. For example, the classification unit 14 may classify each of the abnormal shadows indicating that the property indicated by the property information is a property suspected to be malignant into the same group based on the property group information, and classify each of the abnormal shadows showing properties that are not suspected to be malignant into different groups.

Further, in the above embodiment, a mode in which the feature extraction unit 12 extracts the abnormal shadows extracted from the diagnosis target image has been exemplified, but the user may extract all or some of the abnormal shadows.

Further, as hardware structures of processing units that execute various kinds of processing such as each functional unit of the document creation support apparatus 10 according to the present embodiment, various processors shown below can be used. As described above, the various processors include a programmable logic device (PLD) as a processor of which the circuit configuration can be changed after manufacture, such as a field programmable gate array (FPGA), a dedicated electrical circuit as a processor having a dedicated circuit configuration for executing specific processing such as an application specific integrated circuit (ASIC), and the like, in addition to the CPU as a general-purpose processor that functions as various processing units by executing software (programs).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor for realizing the function of the entire system including a plurality of processing units via one integrated circuit (IC) chip as typified by a system on chip (SoC) or the like is used. In this way, various processing units are configured by using one or more of the above-described various processors as hardware structures.

Furthermore, as the hardware structure of the various processors, more specifically, an electrical circuit (circuitry) in which circuit elements such as semiconductor elements are combined can be used.

The disclosure of Japanese Patent Application No. 2019-217420 filed on Nov. 29, 2019 is incorporated herein by reference in its entirety. Further, all literatures, patent applications, and technical standards described herein are incorporated by reference to the same extent as if the individual literatures, patent applications, and technical standards were specifically and individually stated to be incorporated by reference.

What is claimed is:

1. A document creation support apparatus comprising at least one processor,
wherein the processor is configured to
acquire an image captured through emitting a radiation to a subject;
extract a plurality of shadows suspected of having a disease as a plurality of feature portions from the image by inputting the acquired image to a machine learning model;
analyze each of the feature portions in the image using the machine learning model to derive a property of each of the plurality of feature portions;
automatically generate a first text describing the property of the feature portion for each of the plurality of feature portions included in the image;
classify the plurality of feature portions into at least one group based on the property of each of the plurality of feature portions;
automatically generate a second text integrating the first text generated for each of the feature portions belonging to the same group for describing each group based on text that is common between the first text corresponding to each of the feature portions, wherein the second text reduces a number of characters as compared to the first text; and
generate a third text integrating the second text generated for each group for describing the acquired image based on text that is common between the second text corresponding to each group, wherein the third text further reduces the number of characters for describing the acquired image with respect to the second text, wherein the third text is generated by using common words between the second texts.

2. The document creation support apparatus according to claim 1, wherein the processor performs control such that the first text generated for the feature portion belonging to a designated group is displayed according to the designation of any of the groups.

3. The document creation support apparatus according to claim 2, wherein the processor performs control such that in a case where a description regarding any of the groups in descriptions included in the third text is designated, the first text generated for the feature portion belonging to the designated group is displayed.

4. The document creation support apparatus according to claim 2, wherein the processor performs control such that in a case where any of the plurality of feature portions is designated, the first text generated for the designated feature portion and the first text generated for other feature portions belonging to the same group as the designated feature portion are displayed.

5. The document creation support apparatus according to claim 1, wherein the processor is configured to generate a common portion of each description of the first text generated for each of the feature portions belonging to the same group as the second text.

6. The document creation support apparatus according to claim 1, wherein the processor is configured to classify the plurality of feature portions based on a position where each of the plurality of feature portions is present.

7. The document creation support apparatus according to claim 6, wherein the processor is configured to classify the plurality of feature portions based on an area of an organ in which each of the plurality of feature portions is present.

8. The document creation support apparatus according to claim 1, wherein the processor is configured to acquire disease information indicating a disease corresponding to the feature portion for each of the plurality of feature portions, and classify the plurality of feature portions based on the disease information.

9. The document creation support apparatus according to claim 1, wherein the processor is configured to acquire property information indicating the property of the feature portion for each of the plurality of feature portions, and classify the plurality of feature portions based on the property information.

10. The document creation support apparatus according to claim 1, wherein the processor is further configured to
generate an interactive interface displaying the image having the feature portions and the third text;
detect a position of a pointer in a display area of a display;
load the first text corresponding to the third text from a memory and display the first text in the display area according to the position of the pointer and a link embedded at a first region of the display area, wherein the third text is displayed at the first region, and the first region is embedded with the link of first text.

11. The document creation support apparatus according to claim 1, wherein the processor is further configured to
generate an interactive interface displaying the image having the feature portions and the third text;
detect a position of a pointer in a display area;
load the first text corresponding to a first feature portion among the plurality of feature portions from a memory and display the first text in the display area according to the position of the pointer and a link embedded at a first region of the display area, wherein the first feature portion is displayed at the first region, and the first region is embedded with the link of first text.

12. A document creation support method comprising:
acquiring an image captured through emitting a radiation to a subject;
extracting a plurality of shadows suspected of having a disease as a plurality of feature portions from the image by inputting the acquired image to a machine learning model;
analyzing each of the feature portions in the image using the machine learning model to derive a property of each of the plurality of feature portions;
automatically generating a first text describing the property of the feature portion for each of the plurality of feature portions included in the image;
classifying the plurality of feature portions into at least one group based on the property of each of the plurality of feature portions;
automatically generating a second text integrating the first text generated for each of the feature portions belonging to the same group for describing each group based on text that is common between the first text corresponding to each of the feature portions, wherein the second text reduces a number of characters as compared to the first text; and
generating a third text integrating the second text generated for each group for describing the acquired image based on text that is common between the second text corresponding to each group, wherein the third text further reduces the number of characters for describing the acquired image with respect to the second text, wherein the third text is generated by using common words between the second texts.

13. A non-transitory computer-readable storage medium storing a program for causing a computer to execute a process comprising:

acquiring an image captured through emitting a radiation to a subject;

extracting a plurality of shadows suspected of having a disease as a plurality of feature portions from the image by inputting the acquired image to a machine learning model;

analyzing each of the feature portions in the image using the machine learning model to derive a property of each of the plurality of feature portions;

automatically generating a first text describing the property of the feature portion for each of the plurality of feature portions included in the image;

classifying the plurality of feature portions into at least one group based on the property of each of the plurality of feature portions;

automatically generating a second text integrating the first text generated for each of the feature portions belonging to the same group for describing each group based on text that is common between the first text corresponding to each of the feature portions, wherein the second text reduces a number of characters as compared to the first text; and generating a third text integrating the second text generated for each group for describing the acquired image based on text that is common between the second text corresponding to each group, wherein the third text further reduces the number of characters for describing the acquired image with respect to the second text, wherein the third text is generated by using common words between the second texts.

* * * * *